(12) United States Patent
Wickham et al.

(10) Patent No.: US 11,672,607 B2
(45) Date of Patent: Jun. 13, 2023

(54) SYSTEMS, DEVICES, AND METHODS FOR SURGICAL NAVIGATION WITH ANATOMICAL TRACKING

(71) Applicant: Warsaw Orthopedic, Inc., Warsaw, IN (US)

(72) Inventors: Jeffrey N. Wickham, Ooltewah, TN (US); Nikita Pandey, Broomfield, CO (US); James B. Kelley, Thronton, CO (US); Jerald Redmond, Germantown, TN (US); Mark Dace, Collierville, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 259 days.

(21) Appl. No.: 16/540,881

(22) Filed: Aug. 14, 2019

(65) Prior Publication Data
US 2021/0045813 A1 Feb. 18, 2021

(51) Int. Cl.
*A61B 34/20* (2016.01)
*A61B 34/30* (2016.01)

(52) U.S. Cl.
CPC .............. *A61B 34/20* (2016.02); *A61B 34/30* (2016.02); *A61B 2034/2051* (2016.02); *A61B 2034/2063* (2016.02); *A61B 2034/2065* (2016.02)

(58) Field of Classification Search
USPC ......................................................... 600/424
See application file for complete search history.

(56) References Cited

U.S. PATENT DOCUMENTS

| | | | |
|---|---|---|---|
| 5,592,939 A | 1/1997 | Martinelli |
| 5,913,820 A | 6/1999 | Bladen et al. |
| 5,983,126 A | 11/1999 | Wittkampf |
| 6,474,341 B1 | 11/2002 | Hunter et al. |
| 6,940,941 B2 | 9/2005 | Gregerson et al. |
| 7,001,045 B2 | 2/2006 | Gregerson et al. |
| 7,106,825 B2 | 9/2006 | Gregerson et al. |
| 7,108,421 B2 | 9/2006 | Gregerson et al. |
| 7,188,998 B2 | 3/2007 | Gregerson et al. |
| 7,751,865 B2 | 7/2010 | Jascob et al. |

(Continued)

FOREIGN PATENT DOCUMENTS

KR 10-2014-0112207 A 9/2014

OTHER PUBLICATIONS

StealthStation™ S8 Spinal Navigation Solution, Medtronic PLC Brain Therapies, UC201909309 EN, PMD022116-1.0, © 2019 Medtronic.

(Continued)

*Primary Examiner* — Christopher Koharski
*Assistant Examiner* — Renee C Langhals
(74) *Attorney, Agent, or Firm* — Fox Rothschild LLP (57) ABSTRACT

An approach is provided for image guided procedures. The approach includes acquiring image data of at least one object of a subject, in which the acquired image data is registered to one or more coordinate systems. The approach includes receiving the acquired image data. The approach includes displaying, on one or more smartglasses, one or more superimposed images over a portion of the subject. The one or more superimposed images may be related to the acquired image data. The approach includes aligning the one or more superimposed images to correspond with a position of the at least one object.

18 Claims, 6 Drawing Sheets

(56) References Cited

U.S. PATENT DOCUMENTS

| | | |
|---|---|---|
| 2005/0085714 A1 | 4/2005 | Foley et al. |
| 2016/0000515 A1* | 1/2016 | Sela .................. A61B 90/39 |
| | | 600/424 |
| 2016/0166335 A1 | 6/2016 | Roger et al. |
| 2016/0225192 A1* | 8/2016 | Jones .................. G06F 3/012 |
| 2016/0324580 A1* | 11/2016 | Esterberg .............. A61B 34/10 |
| 2017/0202633 A1 | 7/2017 | Liu |
| 2018/0092699 A1* | 4/2018 | Finley .................. A61B 34/20 |
| 2018/0140362 A1* | 5/2018 | Cali .................... A61B 34/20 |
| 2018/0158113 A1 | 6/2018 | Bisson et al. |
| 2018/0303558 A1* | 10/2018 | Thomas ................ A61B 34/20 |
| 2019/0117318 A1* | 4/2019 | Charron .............. A61B 5/0077 |
| 2020/0221974 A1* | 7/2020 | Singh .................. A61B 34/25 |
| 2021/0304423 A1* | 9/2021 | Yi ...................... A61B 34/20 |

OTHER PUBLICATIONS

The Clinical and Economic Benefits of Using StealthStation® Navigation and O-arm® Imaging Systems for Spine Surgery, Medtronic Surgical Technologies, UC2014181 EN © 2014 Medtronic, Inc. PMD013694-1.0.

StealthStation® S7® Treatment Guidance System Manual, Part No. 9733782, revsion 14, © 2007-2012 Medtronic Navigation, Inc., 74 pp.

International Written Opinion and Search Report, PCT/US2020/045109, dated Nov. 17, 2020.

\* cited by examiner

SYSTEMS, DEVICES, AND METHODS FOR SURGICAL NAVIGATION WITH ANATOMICAL TRACKING

BACKGROUND

Image based surgical techniques have been used to aide physicians in performing a wide variety of delicate surgical procedures. These surgical procedures are used, for example, when a patient's anatomy obscures the visualization of a surgical tool, or when the surgical tool is visible but the patient's anatomy may be difficult to visualize in three dimensions. Such surgical procedures include, for example, spinal implant placement, the alignment of broken bone fragments, and the fixation of bone fractures.

Surgical navigation and robotic systems may use x-ray images or virtual fluoroscopy to visualize positioning a surgical tool within the patient's anatomy. By repeatedly acquiring x-ray images during a surgical procedure, the placement of the surgical tool relative to the patient's anatomy can be displayed in real-time. Additionally, virtual fluoroscopically-based surgical navigation systems may track a trajectory of the surgical tool and superimpose a representation of the surgical tool onto pre-acquired images of the patient's anatomy without requiring x-rays to be repeatedly taken during the surgical procedure.

However, the accuracy of the surgical navigation and robotic systems may be affected by a variety of unaccounted for factors. For example, a patient may re-position his or her body on the surgical table; the surgeon and/or surgical team may inadvertently move the patient; and/or the surgical procedure may cause the patient's anatomy to move, all of which may compromise the accuracy of navigating surgical tools within a patient's anatomy. Moreover, a user operating the surgical tool may have to view the trajectory of the surgical tool on monitors positioned away from the surgical site. Therefore, the user is not directly looking at the surgical site as the user performs the surgical procedure.

SUMMARY

The present disclosure relates generally to image guided medical procedures. More particularly, the present disclosure relates to performing image guided medical procedures via surgical navigation systems, devices, and methods with anatomical tracking.

In one or more cases, the disclosed technology relates to a system for image guided procedures. In one or more cases, the system includes one or more smartglasses or an imaging device configured to acquire image data of at least one object of a subject. In one or more cases, the system includes a navigation system configured to register the acquired image data to one or more coordinate systems. In one or more cases, the one or more smartglasses are further configured to display one or more superimposed images over a portion of the subject. In one or more cases, the one or more superimposed images may be related to the acquired image data. In one or more cases, the one or more smartglasses are further configured to align the one or more superimposed images to correspond with a position of the at least one object.

In one or more cases, the disclosed technology relates to a method for image guided procedures. In one or more cases, the method includes acquiring image data of at least one object of a subject. In one or more cases, the acquired image data may be registered to one or more coordinate systems. In one or more cases, the method includes receiving the acquired image data. In one or more cases, the method includes displaying, on one or more smartglasses, one or more superimposed images over a portion of the subject. In one or more cases, the one or more superimposed images may be related to the acquired image data. In one or more cases, the method includes aligning the one or more superimposed images to correspond with a position of the at least one object.

In one or more cases, the disclosed technology relates to a computer program product. In one or more cases, the computer program product includes a non-transitory computer-readable storage medium having program instructions embodied therewith for image guided procedures, in which the program instructions are executable by one or more processors. In one or more cases, the program instructions include acquiring image data of at least one object of a subject. In one or more cases, the acquired image data may be registered to one or more coordinate systems. In one or more cases, the program instructions include receiving the acquired image data. In one or more cases, the program instructions include displaying, on one or more smartglasses, one or more superimposed images over a portion of the subject. In one or more cases, the one or more superimposed images may be related to the acquired image data. In one or more cases, the program instructions include aligning the one or more superimposed images to correspond with a position of the at least one object.

The foregoing and other objects, features and advantages of the invention will be apparent from the following more particular descriptions of exemplary embodiments of the invention as illustrated in the accompanying drawings wherein like reference numbers generally represent like parts of the disclosure.

BRIEF DESCRIPTION OF DRAWINGS

The following drawings are illustrative of particular embodiments of the present disclosure and therefore do not limit the scope of the present disclosure. The drawings are not to scale and are intended for use in conjunction with the explanations in the following detailed description.

DETAILED DESCRIPTION

The following discussion omits or only briefly describes certain conventional features related to navigation systems, which are apparent to those skilled in the art. It is noted that various embodiments are described in detail with reference to the drawings, in which like reference numerals represent like parts and assemblies throughout the several views. Reference to various embodiments does not limit the scope of the claims appended hereto. Additionally, any examples set forth in this specification are intended to be non-limiting and merely set forth some of the many possible embodiments for the appended claims. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

Embodiments of the present disclosure relate generally, for example, to systems, devices, and methods for image guided medical procedures. More particularly, embodiments of the present disclosure relate to surgical navigation systems, devices, and methods with anatomical tracking for performing image guided medical procedures. For example, such surgical navigation systems, devices, and methods may be those used in the FluoroNav™ system, which utilizes the StealthStation® Treatment Guidance Platform, both of which are available from Medtronic Sofamor Danek, Inc. The StealthStation® Treatment Guidance Platform, and in particular the StealthStation® Navigation System, is described in part in the "StealthStation® S7® Treatment Guidance System Manual" published by Medtronic, Inc. in 2012, the "StealthStation™ S8 Spinal Navigation Solution" brochure published by Medtronic, Inc. in 2019, and in "The Clinical and Economic Benefits of Using StealthStation® Navigation and O-arm® Imaging Systems for Spine Surgery" brochure published by Medtronic, Inc. in 2014. Embodiments of the surgical navigation systems, devices, and methods with anatomical tracking are described below with reference to the drawings. Embodiments of the surgical navigation systems, devices and methods described herein may be used in combination with robotic systems, such as, for example, the Mazor X™ Stealth Edition, which is available from Medtronic, Inc.

The subject disclosure is directed to an example of a surgical procedure on a subject, such as a human patient. It is understood, however, that the systems, devices, and methods described herein are merely exemplary and not intended to limit the scope of the claims included herein. In one or more embodiments, it is understood, that the systems, devices, and methods may be incorporated into and/or used, for example, on inanimate objects. The systems, devices, and methods may be used to register coordinate systems between two systems for use on manufacturing systems, maintenance systems, and the like, and display images related to such registered coordinate systems. For example, an automotive assembly may use one or more of the systems described herein including individual coordinate systems that may be registered together for coordinated or consorted actions, and display images related to such coordinate systems. Accordingly, the exemplary illustration of a surgical procedure herein is not intended to limit the scope of the appended claims.

As discussed herein, various embodiments relate to processes and systems for allowing registration between various coordinate systems and for tracking anatomical objects during image guided procedures. In one or more cases, a first coordinate system may be registered to a second coordinate system. The first coordinate system may be a first tracking space defined by a first tracking system having a first localizer and the second coordinate system may be a second tracking space defined by a second tracking system having a second localizer. Either or both of the first and second coordinate systems may be registered to additional coordinate systems or spaces (e.g. third coordinate system, fourth coordinate system, etc.). The additional coordinate systems may include an image coordinate system or space and/or subject coordinate system or space. As discussed herein, a navigation space or coordinate system may be defined relative to the subject space and by, at least in part, a tracking system space.

Figure 1:
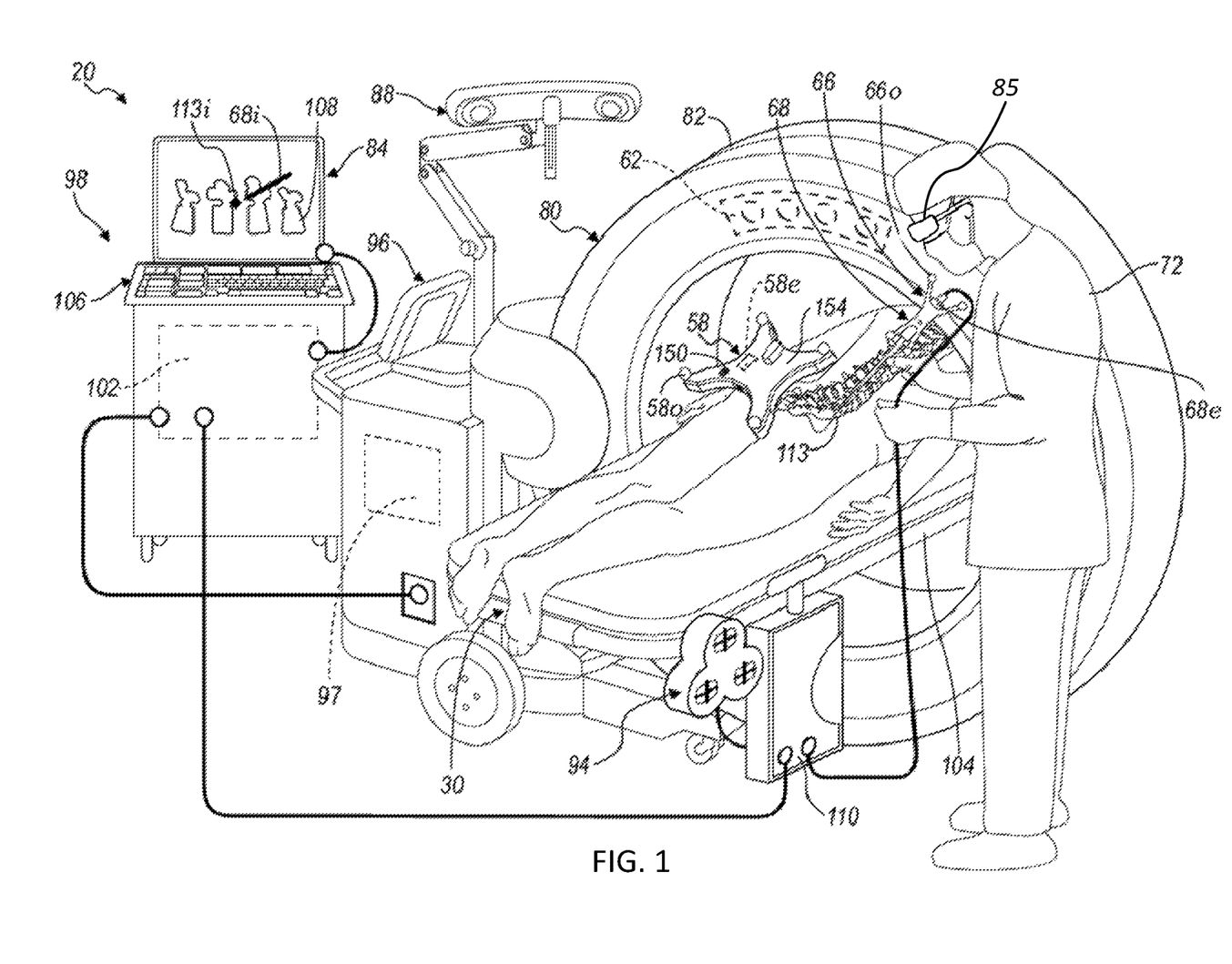
FIG. 1 illustrates an example navigation system.

FIG. 1 illustrates an example navigation system 20 in an operating theater, such as a surgical operating room. Positioned within the surgical theater may be various systems and members to be used during and/or to assist in performing a procedure relative to the subject 30. For example, the navigation system 20 may be positioned within the operating theater. The navigation system 20 may include various elements or portions, such as an optical localizer 88 and an electromagnetic (EM) localizer 94, which define or are used to generate navigation or tracking spaces in one or more selected coordinate systems, such as the first and second coordinate systems, as discussed further herein. The respective localizers 88, 94 may be registered, also referred to as correlated, relative to one another, as discussed further herein, to allow for tracking one or more instruments in either or both of the coordinate systems and relating the tracked position to an additional coordinate system. Accordingly, the navigation system 20 may track one or more tools, such as a tool 68 relative to a subject 30 and/or track plurality of portions or members, such as one or more vertebrae, of the subject 30.

The navigation system 20 may track the location of one or more tracking devices, for example, a subject tracking device 58, an imaging system tracking device 62, a tool tracking device 66, and/or a socket tracking device 185. In one or more cases, the tool 68 attached to the tool tracking device 66 may be any appropriate tool such as a drill, forceps, or other tool operated by the user 72. The tool 68 may also include an implant, such as a spinal implant or orthopedic implant. In one or more other cases, the tool 68 may be a tracking tool, similar to an Ear, Nose, and Throat ("ENT") Registration Probe, an ENT Straight Probe, or an ENT Touch and Go Probe, all of which are available from Medtronic, Inc . . . It should further be noted that the navigation system 20 may be used to navigate any type of tool, implant, or delivery system, including: guide wires, arthroscopic systems, orthopedic implants, spinal implants, deep brain stimulation (DBS) probes, etc. Moreover, the tools may be used to navigate or map any region of the body. The navigation system 20 and the various tools may be used in any appropriate procedure, such as one that is generally minimally invasive or an open procedure.

An imaging device 80 may be used to acquire pre-operative, intra-operative, post-operative, or real-time image data of a subject, such as the subject 30. It should be noted that any portion of the subject 30 may be imaged and any appropriate procedure may be performed relative to the subject. In the example shown, the imaging device 80 comprises an O-arm® imaging device. The imaging device 80 may have a generally annular gantry housing 82 in which an image capturing portion is moveably placed. The imaging device 80 may acquire image data with x-rays. The image capturing portion may include an x-ray source or emission portion and an x-ray receiving or image receiving portion located generally or as practically possible 180 degrees from each other and mounted on a rotor relative to a track or rail. The image capturing portion can be operable to rotate 360 degrees during image acquisition. The image capturing portion may rotate around a central point or axis, allowing image data of the subject 30 to be acquired from multiple directions or in multiple planes. The imaging device 80 may include those disclosed in U.S. Pat. Nos. 7,188,998; 7,108,421; 7,106,825; 7,001,045; and 6,940,941; all of which are incorporated herein in their entirety by reference, or any appropriate portions thereof. For example, the imaging device 80 may utilize flat plate technology having a 1,720 by 1,024 pixel viewing area.

The position of the imaging device 80 and/or portions therein, such as the image capturing portion, may be precisely known relative to any other portion of the imaging device 80. The imaging device 80, according to one or more cases, may determine and recall precise coordinates relative to a fixed or selected coordinate system. This allows the imaging device 80 to know its position relative to the subject 30 or other references. In addition, as discussed herein, the precise knowledge of the position of the image capturing portion can be used in conjunction with a tracking system to determine the position of the image capturing portion and the image data relative to the tracked subject 30, such as the patient 30.

In one or more cases, a tracking device 62 may track the imaging device 80. The image data defining an image space acquired of the patient 30 may, according to one or more cases, be inherently or automatically registered relative to an object space. The object space can be the space defined by one or more objects, for example, one or more vertebra, of the patient 30 in the navigation system 20. The automatic registration may be achieved by including the tracking device 62 on the imaging device 80 and/or the determinable precise location of the image capturing portion. In one or more cases, as discussed herein, imageable portions, virtual fiducial points and other features can also be used to allow for registration, automatic or otherwise. It should be noted that image data can be acquired of one or more objects of any subject which will define subject space. Patient space is an exemplary subject space. Registration allows for a translation between patient space and image space.

The imaging device 80 may track the patient 30 as the patient 30 moves with a patient tracking device (also referred to as a dynamic reference frame (DRF)) or subject tracking device 58. Alternatively, or in addition thereto, the patient 30 may be fixed within navigation space defined by the navigation system 20 to allow for registration. As discussed herein, registration of the image space to the patient space or subject space allows for navigation of the tool 68 with the image data. In one or more cases, when navigating the tool 68, a display device 84 may display a position of the tool 68 relative to image data acquired of the patient 30. In addition to or in one or more other cases, when navigating the tool 68, one or more smartglasses, such as the smartglasses 85 worn by the user 72, may display a position of the tool 68 relative to image data acquired of the patient 30. Various tracking systems, such as one including the optical localizer 88 or the electromagnetic (EM) localizer 92 may track the tool 68.

Figure 4A:
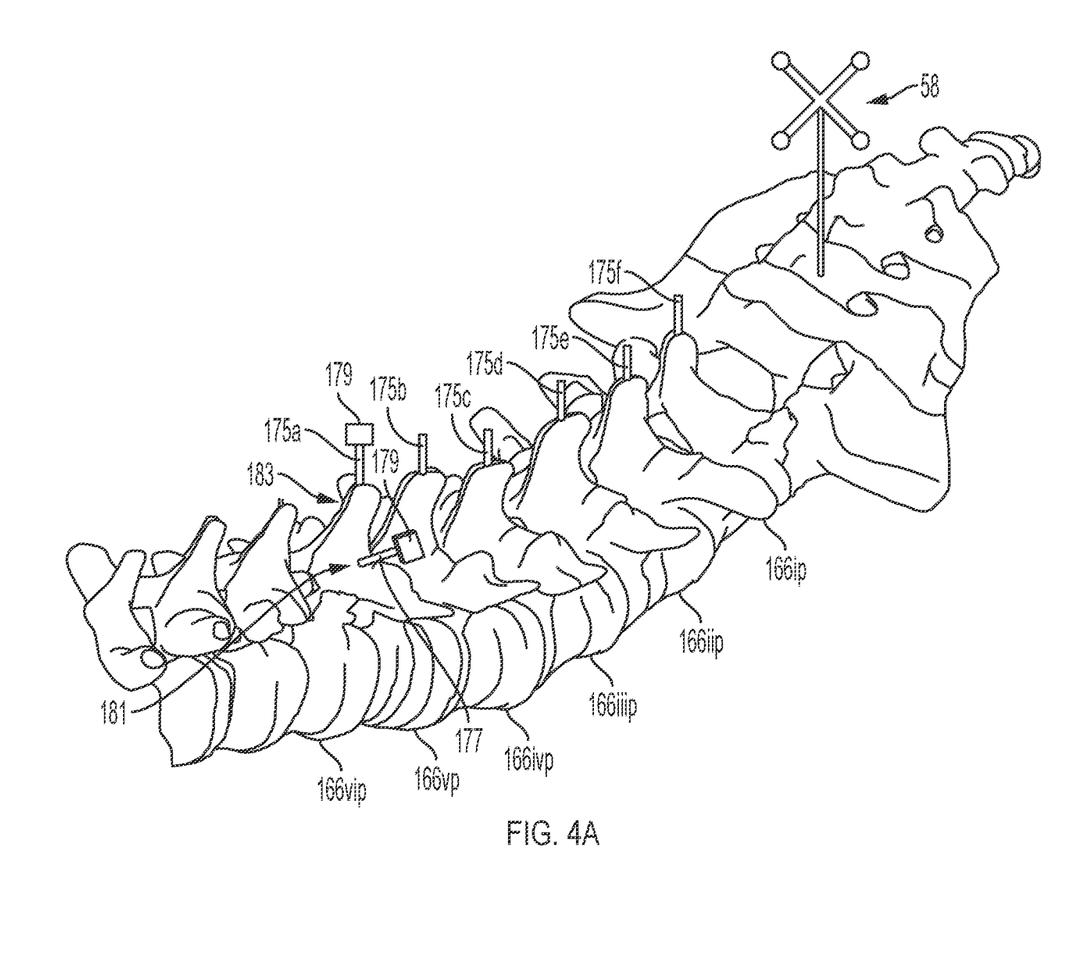
FIG. 4A illustrates an example of one or more sockets coupled with one or more objects, respectively, and one or more trackers coupled to the one or more sockets.
Figure 4B:
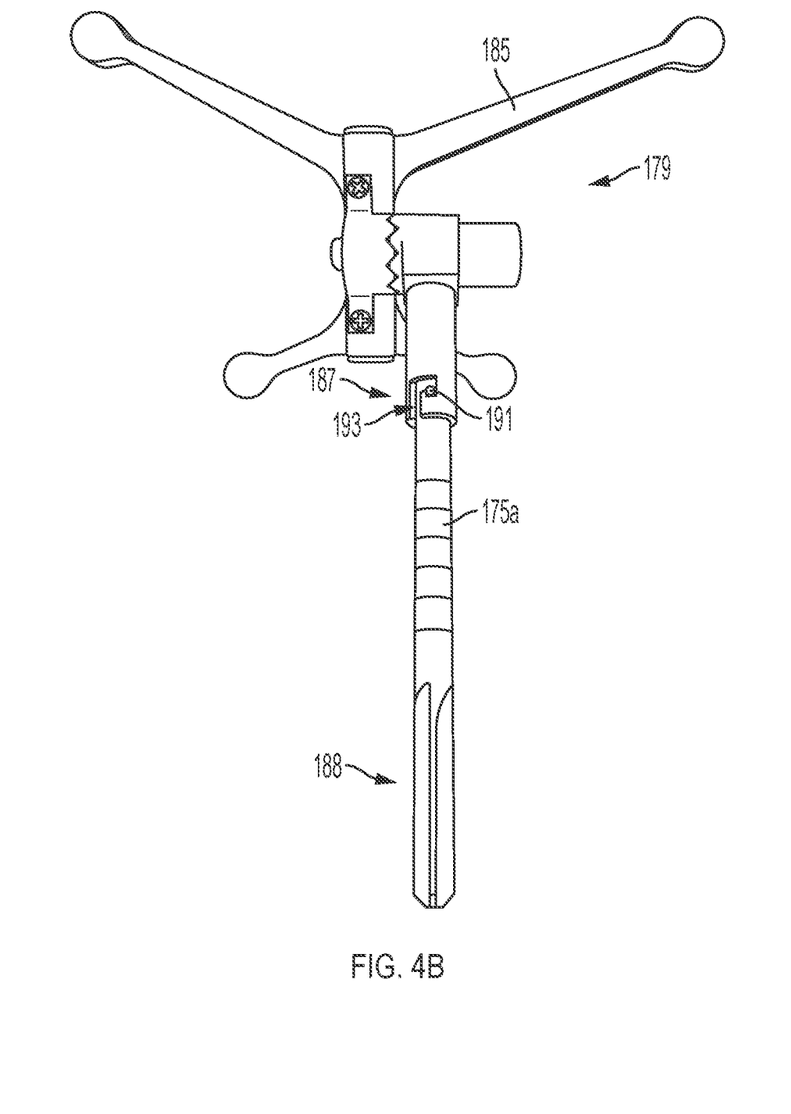
FIG. 4B illustrates an example tracker coupled with an example socket.
Figure 4C:
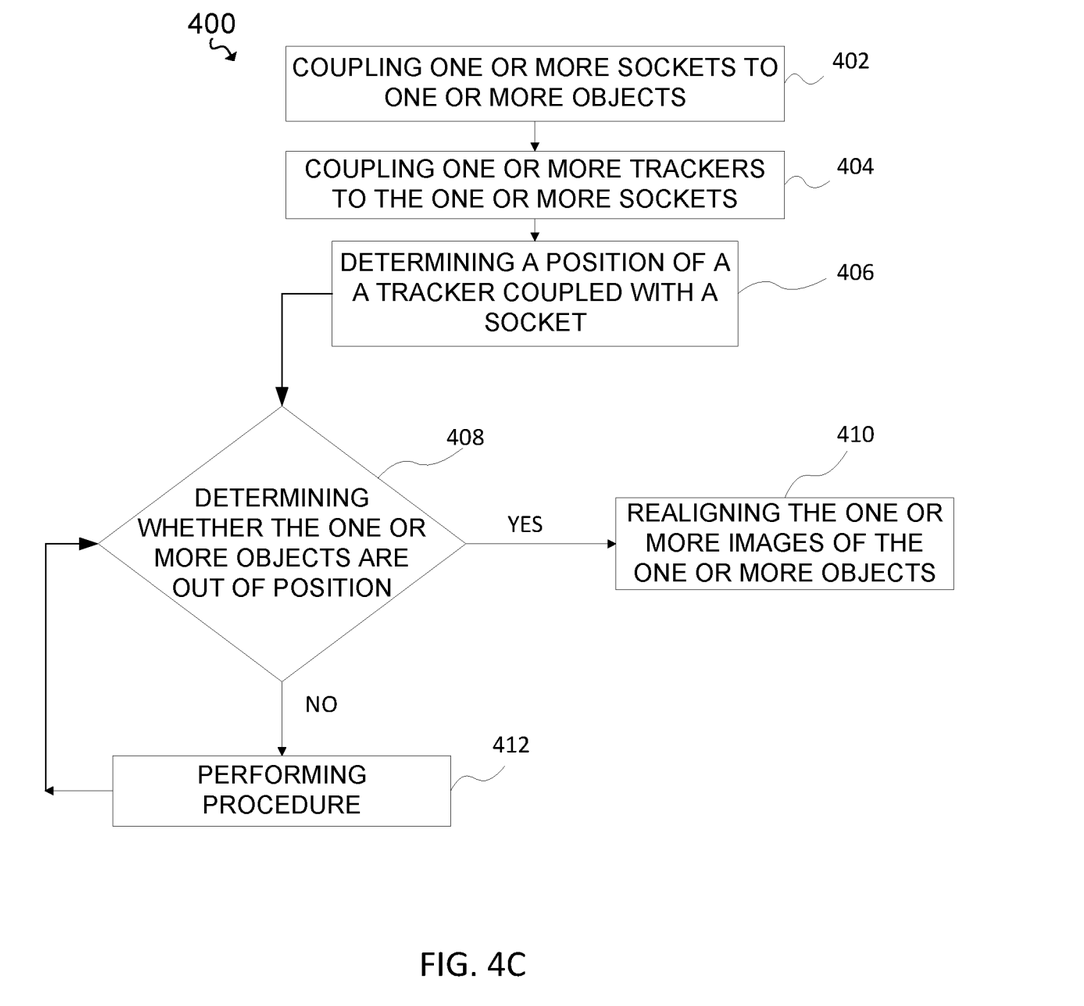
FIG. 4C is a flowchart illustrating an example alignment method.

More than one tracking system can be used to track the tool 68 and/or sockets, such as the sockets 175a, 175b, 175c, 175d, 175e, and 175f discussed in FIG. 4A-4C, in the navigation system 20. In one or more cases, the tracking system may include an electromagnetic tracking (EM) system having the EM localizer 94 and/or an optical tracking system having the optical localizer 88. Either or both of the tracking systems may track selected tracking devices, as discussed herein. In one or more cases, a portion of a tracking device may be tracked with a selected tracking system. A tracking device need not refer to the entire member or structure to which the tracking device is affixed or associated. It is noted that additional or alternative tracking systems may also be used, such as radar, acoustic, ultrasonic, and/or other like tracking systems. The tracking system tracks the tracking device in the tracking or navigation space. The tracking system is able to generate a signal based on the tracking (e.g. within a field of view of a camera, EM field, etc.) and the signal is used within the navigation system to determine the position of the tracked element. In one or more cases, the display device 84 may display the determined position of the tracked element, such as the tool 68 and/or one or more objects of the subject 30, relative to another coordinate system, such as image space. In addition to or in one or more other cases, the smartglasses 85 may display the determined position relative to the other coordinate system, such as image space.

It is further appreciated that the imaging device 80 may be an imaging device other than the O-arm® imaging device and may include in addition or alternatively a fluoroscopic C-arm. Other exemplary imaging devices may include fluoroscopes such as bi-plane fluoroscopic systems, ceiling mounted fluoroscopic systems, cath-lab fluoroscopic systems, fixed C-arm fluoroscopic systems, isocentric C-arm fluoroscopic systems, 3D fluoroscopic systems, etc. Other appropriate imaging devices can also include MRI, CT, ultrasound, etc.

In one or more cases, an imaging device controller 96 may control the imaging device 80 and may receive the image data generated at the image capturing portion and store the images for later use. The controller 96 may include a processor 97 and/or memory. The controller 96 may control the rotation of the image capturing portion of the imaging device 80. It is noted that the controller 96 need not be integral with the gantry housing 82, but may be separate therefrom. For example, the controller 96 may be a portion of the navigation system 20 that may include a processing and/or work station 98 including a processing unit or processing system 102. The controller 96 may be integral with the gantry 82 and may include a second and separate processor 97, such as that in a portable computer.

The patient 30 may be positioned on an operating table 104. In an example, the table 104 can be an Axis Jackson® operating table sold by OSI, a subsidiary of Mizuho Ikakogyo Co., Ltd., having a place of business in Tokyo, Japan or Mizuho Orthopedic Systems, Inc. having a place of business in California, USA. Patient positioning devices may be used with the table, and include a Mayfield® clamp or those set forth in commonly assigned U.S. patent application Ser. No. 10/405,068 entitled "An Integrated Electromagnetic Navigation And Patient Positioning Device", filed Apr. 1, 2003 which is hereby incorporated in its entirety by reference.

The navigation system 20 may determine a position of the patient 30 relative to the imaging device 80 and/or the one or more smartglasses 85. The tracking device 62 may track and locate at least a portion of the imaging device 80, for example the gantry or housing 82. In one or more cases, a subject tracking device 58 may track the patient 30, as discussed further herein. Accordingly, the position of the patient 30 relative to the imaging device 80 can be determined. Further, the location of the imaging portion can be determined relative to the housing 82 due to its position of the imaging portion on the rail within the housing 82. For the cases in which the imaging device 80 is an O-Arm® imaging device, the imaging device 80 may have an accuracy of within 10 microns. Positioning of the imaging portion is further described in U.S. Pat. Nos. 7,188,998; 7,108,421; 7,106,825; 7,001,045; and 6,940,941; all of which are incorporated herein by reference in their entirety In one or more cases, the imaging device 80 can generate and/or emit x-rays from the x-ray source that propagate through the patient 30 and are received by the x-ray imaging receiving portion. The image capturing portion generates image data representing the intensities of the received x-rays. In one or more cases, the image capturing portion may include an image intensifier that first converts the x-rays to visible light and a camera (e.g. a charge couple device) that converts the visible light into digital image data. In one or more other cases, the image capturing portion may also be a digital device that converts x-rays directly to digital image data for forming images, thus potentially avoiding distortion introduced by first converting to visible light.

In one or more cases, the imaging device 80 and/or the one or more smartglasses 85 may take two dimensional and/or three dimensional fluoroscopic image data, which is captured and stored in the imaging device controller 96. Multiple image data may be captured and assembled to provide a larger view or image of a whole region of the patient 30, as opposed to being directed to only a portion of a region of the patient 30. For example, multiple image data of the spine of the patient 30 may be appended together to provide a full view or complete set of image data of the spine. In another example, multiple image data may include bony anatomy, for example, three vertebrae of the patient. In another example, multiple image data may include bony anatomy and tissue surrounding the bony anatomy.

In one or more cases, the image device controller 96 may forward the image data from the image device controller 96 to the navigation computer and/or processor system 102 with memory. The navigation computer and/or processor system 102 may be a part of a work station 98 having a display device 84 and a user interface 106. It is noted that the image data is not necessarily first retained in the controller 96, but may be directly transmitted to the work station 98. The work station 98 may provide facilities for displaying the image data as an image 108 on the display 84, saving the image, digitally manipulating the image, or printing a hard copy image of the received image data. The user interface 106, which may be a keyboard, mouse, touch pen, touch screen, or other suitable device, allows a user, such as the user 72, to provide inputs to control the imaging device 80, via the image device controller 96, or adjust the display settings of the display 84. The work station 98 may direct the image device controller 96 to adjust the image capturing portion of the imaging device 80 to obtain various two-dimensional images along different planes in order to generate representative two-dimensional and/or three-dimensional image data. The workstation 98 may display the two-dimensional and/or three-dimensional image data as two dimensional and/or three dimensional images, respectively, on the display 84.

Figure 3:
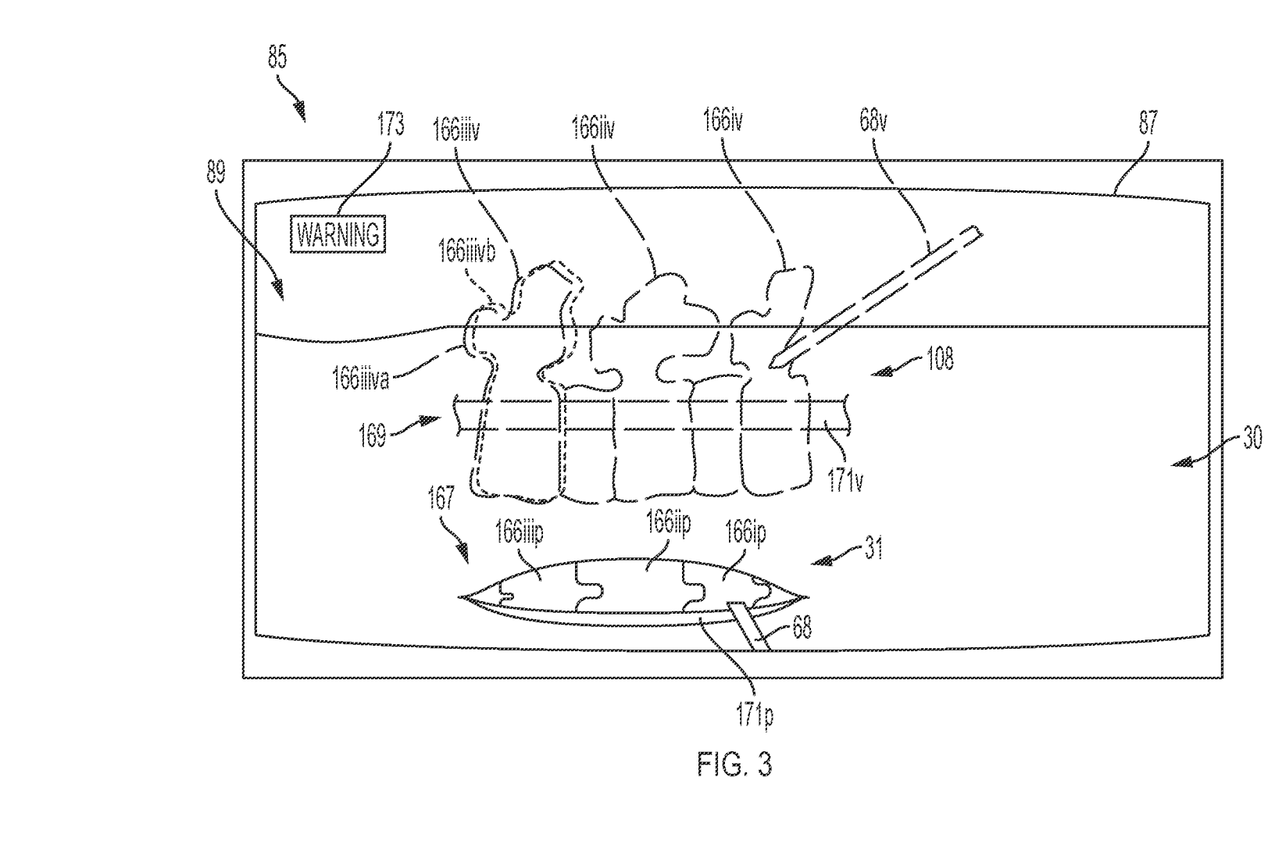
FIG. 3 illustrates an example view of smartglasses, which implement the example method of FIG. 2.

In one or more cases, the work station 98 may transmit the image data to one or more smartglasses, such as smartglasses 85. The work station 98 may transmit the image data to the smartglasses 85, and the smartglasses 85 may display the image data as one or more images on the display 87 of the smartglasses 85 in real-time. In one or more cases, the smartglasses 85 may superimpose the one or more images 108 and/or other information onto a field of view of the user wearing the smartglasses 85. In one or more cases, the display 87 of the smartglasses 85 may be, for example, an optical head mounted display, a transparent heads-up display, an augmented reality display, a virtual reality display, a mixed reality display, or the like. In one or more cases, the smartglasses 85 may acquire image data that defines an image space discussed herein. For example, the smartglasses 85 may acquire image data that defines a spine 167 of a section of the spine 167, as shown in FIG. 3, of a patient. The smartglasses 85 may be connected, wired and/or wirelessly, to the work station 98 and/or navigation system 20 to transmit and receive the image data. The smartglasses 85 may receive the two-dimensional and/or three-dimensional image data from the workstation 98 and/or the navigation system 20, and may display the two-dimensional and/or three-dimensional image data as two dimensional and/or three dimensional images, respectively, on the display 87. The smartglasses 85, according to one or more cases, may determine and recall precise coordinates relative to a fixed or selected coordinate system. This allows the smartglasses 85 to know its position relative to the subject 30 or other references. In addition, as discussed herein, the precise knowledge of the position of the image capturing portion can be used in conjunction with a tracking system to determine the position of the image capturing portion and the image data relative to the tracked subject 30, such as the patient 30. In one or more cases in which multiple smartglasses are used in a procedure, each of the smartglasses may acquire image data that defines the image space and transmit the acquired image data to the navigation system 20. The navigation system 20 may compile the acquired image data from the plurality of smartglasses to determine whether one or more objects within the image space moved, as discussed herein.

In one or more cases, the navigation system 20 may include a tracking system which may be one or both of the electromagnetic (EM) localizer 94 and/or the optical localizer 88. As noted above, more or alternative tracking systems may be provided or used. The tracking systems may include a controller and interface portion 110. The controller 110 can be connected to the processor portion system 102, which may include a processor included within a computer. The controller 110 may be connected to one or more of the localizers, such as the EM localizer 94 and/or the optical localizer 88. The connections may be wired or wireless and allow for single or two-way communication. The EM tracking system may include the STEALTHSTATION®; or can be the EM tracking system described in U.S. Pat. No. 7,751,865, issued Jul. 6, 2010, and entitled "METHOD AND APPARATUS FOR SURGICAL NAVIGATION"; U.S. Pat. No. 5,913,820, entitled "Position Location System," issued Jun. 22, 1999; and U.S. Pat. No. 5,592,939, entitled "Method and System for Navigating a Catheter Probe," issued Jan. 14, 1997; all of which are herein incorporated by reference in their entirety. It is noted that the navigation system 20 may be or include any appropriate tracking system, such as the STEALTHSTATION®, StealthStation™ S8, or the StealthStation® S7®, having an optical localizer, which may be used as the optical localizer 88. Other tracking systems may utilize acoustic, radiation, radar, ultrasonic, or the like.

Wired or physical connections may interconnect the tracking systems, imaging device 80, navigation system 20, and other systems and devices in the operating theater. Alternatively, various portions, such as the tool 68 may employ a wireless communications channel, such as that disclosed in U.S. Pat. No. 6,474,341, entitled "Surgical Communication Power System," issued Nov. 5, 2002, herein incorporated by reference in its entirety, as opposed to being coupled directly to the controller 110. Also, the tracking devices 62, 66, 54 may generate a field and/or signal that is sensed by the localizer(s) 88, 94.

Various portions of the navigation system 20, such as the tool 68, and others as will be described in detail below, may be equipped with at least one, and generally multiple, of the tracking devices 66. The tool 68 may include more than one type or modality of tracking device 66, such as an EM tracking device 66e and/or an optical tracking device 66o. The tool 68 can include a graspable or manipulable portion at a proximal end and the tracking devices may be fixed near the manipulable portion of the instrument 68.

Additional representative or alternative localization and tracking system is set forth in U.S. Pat. No. 5,983,126, entitled "Catheter Location System and Method," issued Nov. 9, 1999, which is hereby incorporated by reference in its entirety. The navigation system 20, therefore, may be a hybrid system that includes components from various tracking systems.

In one or more cases, the navigation system 20 may be used to track the tool 68 relative to the patient 30. The tracking system may track the tool 68, as discussed above. Image data of the patient 30, or an appropriate subject, can be used to assist the user 72 in guiding the tool 68. The image data may be registered to the patient 30. The image data defines an image space that is registered to the patient space defined by the patient 30. The registration may be performed as discussed herein, automatically, manually, or combinations thereof.

Registration allows a translation map to be generated of the physical location of the tool 68 relative to the image space of the image data. The translation map allows the tracked position of the tool 68 to be displayed on the display device 84 relative to the image data, and/or the display 87 of the smartglasses 85 relative to the image data. A graphical representation 68i, displayed on the display device 84 also referred to as an icon, can be used to illustrate the location of the tool 68 relative to the image data. A graphical representation 68v, displayed on the display 87 of the smartglasses 85, can be used to illustrate the location of the tool 68 relative to the image data.

As discussed above, the imaging system 80, the one or more smartglasses 85, or any appropriate imaging system, may acquire images of the subject 30. The images may be automatically registered, according to various procedures such as those known in the art, including tracking the imaging system 80 (e.g. with the image tracking device 62) and tracking the subject 30 with the subject tracking device 58. Other registration processes may include identifying fiducial or correlation points in the image 108 and on the patient or subject 30. Fiducial points may include artificial fiducials that are imageable portions (e.g. radiopaque markers) that are positioned on and/or implanted in the subject 30 during acquisition of images with the imaging device 80 and appear on the image 108, such as a fiducial mark 113. The user 72 may identify the fiducial mark 113 in the image 108 and then also identify the fiducial on the subject 30, such as touching the fiducial in the subject 30 with the tool 68 that is tracked with one or more of the tracking systems. The navigation system 20 may then determine the position of the tracked tool 68 and correlated it with the fiducial 113 identified in the image 108.

In one or more cases, when the fiducial portions 113 are imaged with the imaging device 80, image data is generated that includes or identifies the fiducial portions 113. The fiducial portions 113 can be identified in image data as imaged fiducial portions 113i automatically (e.g. with a processor executing a program), manually (e.g. by selection of an identification by the user 72), or combinations thereof (e.g. by selection of an identification by the user 72 of a seed point and segmentation by a processor executing a program). Methods of automatic imageable portion identification include those disclosed in U.S. Pat. No. 8,150,494 issued on Apr. 3, 2012, incorporated herein by reference in its entirety. Manual identification can include selecting an element (e.g. pixel) or region in the image data wherein the imageable portion has been imaged. Regardless, the fiducial portions 113 identified in the image data can be used as fiducial points or positions that can be used to register the image data or the image space of the image data with patient space.

In one or more cases, to register an image space or coordinate system to another space or coordinate system, such as a navigation space, the fiducial portions 113 that are identified in the image 108 may then be identified in the subject space defined by the subject 30, in an appropriate manner. For example, the user 72 may move the tool 68 relative to the subject 30 to touch the fiducial portions 113, if the fiducial portions are attached to the subject 30 in the same position during the acquisition of the image data to generate the image 108. It is noted that the fiducial portions 113, as discussed above in one or more cases, may be attached to the subject 30 and/or may include anatomical portions of the subject 30.

Additionally, a tracking device, such as socket 175a and a tracker 179 discussed herein, may be incorporated into the fiducial portions 113 and they may be maintained with the subject 30 after the image is acquired. In this case, the registration or the identification of the fiducial portions 113 in a subject space may be made. Nevertheless, in one or more cases, the user 72 may move the tool 68 to touch the fiducial portions 113. The tracking system, such as with the optical localizer 88, may track the position of the tool 68 due to the tracking device 66 attached thereto. This allows the user 72 to identify in the navigation space the locations of the fiducial portions 113 that are identified in the image 108. After identifying the positions of the fiducial portions 113 in the navigation space, which may include a subject space, the translation map may be made between the subject space defined by the subject 30 in a navigation space and the image space defined by the image 108. Accordingly, identical or known locations allow for registration as discussed further herein.

During registration, a translation map is determined between the image data coordinate system of the image data such as the one or more images 108 and the patient space defined by the patient 30. Once the registration occurs, the tracking system may track the tool 68 and register a position of the tracked tool 68 to allow an identification and illustration of the position of the tracked tool 68 as an icon, which may be superimposed on the one or more images 108. Registration of the one or more images 108 (or any selected image data) to the subject 30 may occur at any appropriate time.

After the registration of the image space to the patient space, the instrument 68 may be tracked relative to the one or more images 108. As illustrated in FIG. 1, the icon 68i representing a position (including 3D location and orientation) of the instrument 68 may be displayed relative to the image 108 on the display 84. Due to the registration of the image space to the patient space, the position of the icon 68i relative to the image 108 can substantially identify or mimic the location of the tool 68 relative to the patient 30 in the patient space. As discussed above, this can allow a navigated procedure to occur. It is noted that the graphical representation 68v of the tool 68 may be displayed on the display 87 and operate in the same or similar manner as the icon 68i. Accordingly, a description of such features is not repeated.

In one or more cases, the patient tracker or subject tracking device 58 may also include more than one tracking element or portion and/or be operable with one or more tracking systems. For example, the patient tracker 58 may include one or more optical trackable members or portions, such as a reflective member 58o. It is understood that the optically trackable member may also be an active emitter (e.g. LED) or passive, such as a reflector. Further, the subject tracking device 58 may include an electromagnetic tracking member or portion 58e. The EM tracker 58e may be fixed relative to the optical tracker 58o such that the position (including three-dimensional location and/or one or more degree of freedom orientation) is fixed. Accordingly, the patient tracker 58 may be used as a registration or dynamic reference frame relative to the patient 30 using at least two tracking systems, such as the optical localizer 88 and the EM localizer 94.

The subject tracking device 58 may also be used for registration and/or calibration of tools including the tool 68 with selected fiducial or registration portion 150. The registration portion 150 may include a divot or indent that the instrument 68 may contact to allow the navigation system 20 to determine a distal end or terminal end of the tool 68 relative to the tracking device 66. As discussed above, the tracking device 66 may also be tracked in more than one tracking system including the optical tracking device 66o and the EM tracking device 66e.

It is noted that the multiple portions of the tracking device 66 may be fixed together in a single unit, similar to the trackable member or assembly 154. Alternatively, or in addition thereto, the two tracking devices, such as the optical tracking device 66o and the EM tracking device 66e, may be fixed relative to one another on the tool 68. Accordingly, regardless of the configuration, the position of the EM tracking device 66e relative to the optical tracking device 66o is fixed for a selected procedure, such as a procedure on the subject 30.

Figure 2:
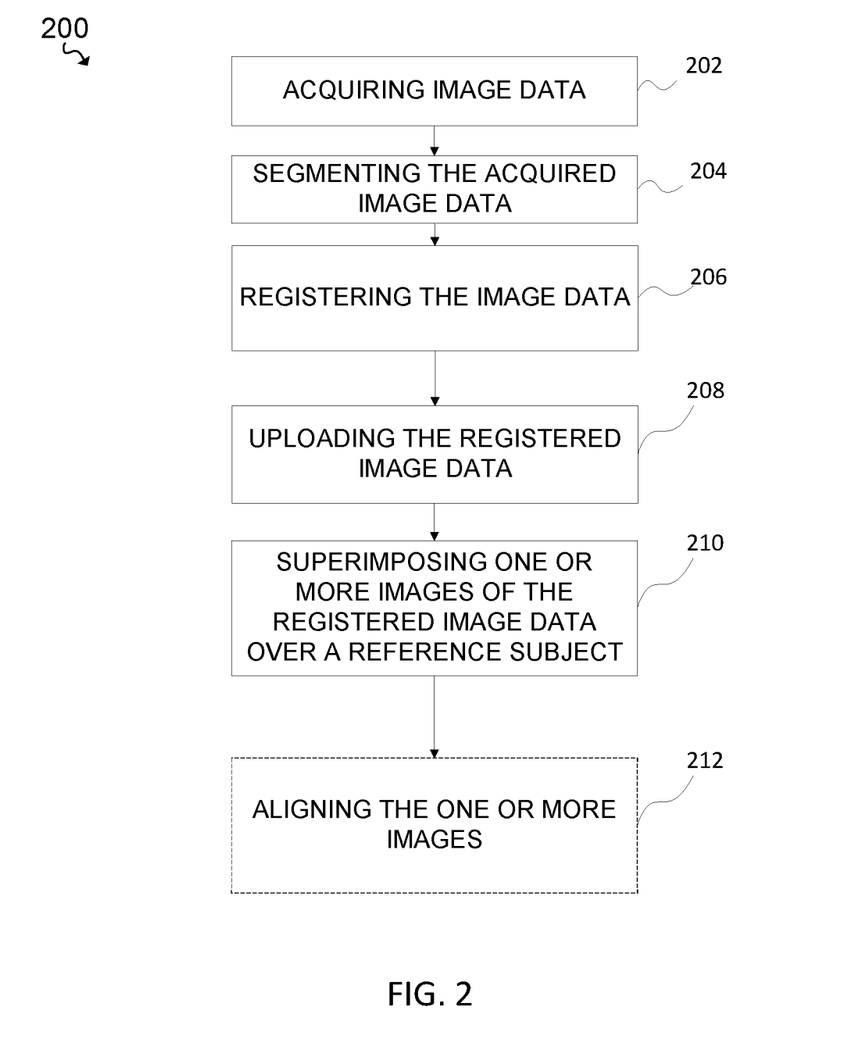
FIG. 2 is a flowchart illustrating an example method of a navigation procedure.

FIG. 2 is a flowchart illustrating an example method of a navigation procedure 200. FIG. 3 illustrates an example view of the smartglasses 85, which implements the example method of FIG. 3.

In one or more cases, image data is acquired at 202. The image data may be preferably acquired by the imaging device 80 and/or one or more smartglasses 85, as discussed herein. In one or more cases, the image data may define an image space acquired of the subject 30, such as the patient. For example, the imaging device 80 may acquire image data that defines a spine 167 or section of the spine 167 of the patient. That is, in one or more cases, the acquired image data may include the bony anatomy of the spine, such as the vertebrae, the tissue surrounding the bony anatomy, or the bony anatomy and the tissue surrounding the bony anatomy. In another example, the imaging device 80 may acquire image data that defines other portions of the bony anatomy, such as a foot or hand, and one or more of the surrounding tissue of the patient 30. In another example, one or more smartglasses 85 may acquire the image data by scanning the image space, such as the surgical site. The one or more smartglasses 85 may transmit the acquired image data to the navigation system 20. The navigation system 20 may compile the acquired image data received from the one or more smartglasses 85. In yet another example, the imaging device 80 and the one or more smartglasses 85 may acquire the image data by scanning the image space, and transmit the acquired image data to the navigation system 20.

The image data may be preferably acquired pre-operatively. The image data may be acquired at multiple times prior to performing an operation. The image data may be acquired prior to positioning the patient 30 in the operating theater relative to the navigation system 20. In one or more cases, the imaging device 80 and/or the one or more smartglasses 85 may obtain various two-dimensional images along different planes and generate two-dimensional and/or three-dimensional image data.

In one or more cases, the acquired image data may be segmented at 204. The acquired image data may be preferably segmented by the workstation 98. Portions of the image data may be segmented. For example, when the imaging device 80 and/or the one or more smartglasses 85 acquire image data that define the spine 167 or a section of the spine 167 of the patient 30, the work station 98 may segment the image data corresponding to each vertebra, such as vertebra 166ip, vertebra 166iip, and vertebra 166iiip, of the spine 167. The image data of each vertebra may be segmented in any appropriate manner, such as in a substantially automatic process, manual process, or a combination of manual and automatic processes. The segmentation of the vertebrae image data may include segmentation such as that used by the Mazor X® Robotic system to segment image data of the vertebrae or other appropriate segmentation techniques. A manual segmentation technique may include the user 72 outlining or defining the portions of the image relating to selected portions, such as the first vertebra 166ip, the second vertebra 166iip, and the third vertebra 166iiip. An automatic segmentation technique may include a processor, such as the processor 102, executing an algorithm to segment the vertebrae in the image. A semi-manual segmentation technique may include the user 72 identifying a seed pixel or voxel or multiple seed pixels or voxels and the processor system 102 executing instructions to segment image data that are related to the identified seed portions. In one or more cases, the segmentation of the image data may include segmenting one or more edges or boundaries of respective portions, such as the boundaries of a vertebra, and/or identifying appropriate or selected portions, such as identifying endpoints and determining lines or planes relative thereto.

In one or more cases, the image data may be registered at 206. The image data that was acquired and/or the segmented may be preferably registered by the navigation system 20, as discussed herein. In one or more cases, the navigation system 20 may register image data to one or more coordinate systems. For example, the navigation system 20 may register image data to a first coordinate system and a second coordinate system of the optical tracking system. The navigation system 20 may use the patient tracker 58 to correlate the first coordinate system, and may use the tool tracking device 66 to correlate the second coordinate system. In another example, the navigation system 20 may register image data to a first coordinate system of the optical localizer 88 and a second coordinate system of the EM localizer 94. The image data may be registered in the first coordinate system which may be defined by the optical localizer 88. It is understood that the first coordinate system may be any appropriate coordinate system, and reference to optical localizer 88 is merely for example. The image data may be registered in the second coordinate system which may be defined by the EM localizer 94. The EM localizer 94 may also be used to define a navigation or tracking space relative to the subject 30. It is understood that the second coordinate system may be any appropriate coordinate system, and reference to EM localizer 94 is merely for example. Having registered the image data, the navigation system 20 correlates the first coordinate system and the second coordinate system. For the cases in which the patient tracker 58 includes the EM tracking device 58e and the optical tracking device 58o, the navigation system 20 may use the patient tracker 58 to correlate the first coordinate system of the optical localizer 88 and the second coordinate system of the EM localizer 94.

In one or more cases, the patient tracker 58 may include the EM tracking device 58e and the optical tracking device 58o to provide to a single fixed point, also referred to as a reference point. Accordingly, registration of either one of the portions, such as the optical tracking portion 58o to the image data may be then used to correlate the single point to the second coordinate system of the EM tracking system due to the EM tracking device 58e fixed relative to the same point. It is understood, therefore, that additional tracking devices may also be associated with the patient tracker 58. For example, a radar tracking device may also be associated with the patient tracker 58 to allow for correlation to a radar tracking system which may define a third coordinate system.

Having registered the acquired image data and the segmented image data, the registered image data may be uploaded at 208. In one or more cases, the registered image data may be uploaded, preferably by the work station 98. In one or more cases, the work station 98 may upload the registered image data to the display 84 of the work station 98. In one or more other cases, the work station 98 may upload the registered image data to the one or more smartglasses, such as smartglasses 85. In yet one or more other cases, the work station 98 may upload the registered image data to the display 84 and the one or more smartglasses 85.

In one or more cases, one or more images 108 of the registered image data may be superimposed over a reference subject 30 at 210. The one or more images 108 may be preferably superimposed over the reference subject 30 by the smartglasses 85. The smartglasses 85 may superimpose one or more images, such as image 108, onto a field of view 89 of the user, such as user 72, wearing the smartglasses 85. For example, the smartglasses 85 may superimpose images 108 over the back 31 of the patient 30. As illustrated in FIG. 3, the back 31 of the patient 30 may represent a field of view 89 of the user 72. The images 108 may include, for example, a tool 68v, vertebra 166iv, vertebra 166iiv, and 166iiiv. The smartglasses 85 may display the one or more images 108 of the registered image data on the display 87 of the smartglasses 85. The one or more images 108 of the registered image data may be displayed on the display 84 of the work station 98.

In one or more cases, the smartglasses 85 may display the one or more images 108 as being translucent, semi-translucent, or opaque. In cases in which the image data is segmented, the smartglasses 85 may display the segmented images in a combination of effects. For example, the smartglasses 85 may display the tool 68v with an opaque effect, and the vertebrae 166iv, 166iiv, and 166iiiv with a translucent effect. Moreover, the smartglasses 85 may display the one or more images 108, either being segmented or not segmented, with an effect that is based on user selection. For example, the user 72 may select an option provided by the work station 98, the smartglasses 85, and/or the navigation system 20 to display the one or more images 108 with a semi-translucent effect.

In one or more cases, the one or more images 108 may be displayed as two dimensional images and/or three dimensional images. In one or more cases, the one or more images 108 may be positioned on an axis, which is fixed to the subject, such that as the field of view 89 changes, the one or more images 108 do not rotate on the axis and the view of the one or more images 108 changes corresponding to the new field of view of the user. For example, if the one or more images 108 are fixed on an axis such that a front view of the one or more images 108 are displayed in the initial field of view 89, then as the user 72 changes the field of view 89, for example, to see a side of the one or more images 108, the smartglasses 85 display the side of the one or more images 108 corresponding to the subsequent field of view. The smartglasses 85 may display the changing of views of the one or more images dynamically and/or in real-time. In one or more other cases, the one or more images 108 may be displayed in a static position such that the same positional view of the one or more images 108 is displayed regardless of whether or not the field of view 89 changes. For example, if the one or more images 108 are displayed in a front view, then as the field of view 89 changes, the one or more images 108 rotate such that the front view of the images are shown in different field of view 89. In one or more cases, the smartglasses 85 may dynamically display in real-time one or more images 108 to correspond to the movement of the object of the registered image data. For example, the smartglasses 85 may display the insertion of the tool 68 into the vertebra 166ip by displaying the image of the tool 68v being inserted into the image of the vertebra 166iv.

In one or more cases, the one or more images 108 may be pinned to a viewing location 169 on the subject 30. As the user 72 moves his or her head to view another part of the patient's body or another part of the surgical theater, i.e., as the user 72 changes the field of view 89, the one or more images 108 remain fixed with the viewing location 169 and disappear from the display 87 as the field of view 89 is changed to another field of view. In one or more other cases, the one or more images 108 may pinned to a location on the display 87. The location may be for example, a right or left area of the display 87, a top or bottom area of the display 87, a corner area of the display 87, or a central area of the display 87. As the user 72 changes the field of view 89, for example, by looking at another person in the surgical theater, the one or more images 108 may remain fixed in the location, for example, an upper left corner, of the display 87.

Having superimposed the one or more images over the reference subject 30, the one or more images may be optionally aligned at 212.

In one or more cases, subsequent to registering the image data and/or during a procedure, a user, such as the user 72, may select one or more images to realign and/or make fine adjustments. For example, the user 72 may select the image of the vertebra 166iiiv to realign. In one or more cases, the user 72 may identify one or more fiducial or correlation points in the image of the vertebra 166iiiv by selecting the one or more fiducial points on the vertebra 166iiiv using the tool 68.

Either before or after identifying the one or more fiducial points in the image of the vertebra 166iiiv, the user 72 may identify one or more fiducial points on the vertebra 166iiip of the section of the spine 167, such as by touching the surface of the vertebra 166iiip with the tool 68 and thereby creating a constraint point. By touching the surface of the vertebra 166iiip, the navigation system 20 constrains the surface of the image of the vertebra 166iiiv to the constraint point, and moves the image of the vertebra 166iiiv such that the image of the vertebra 166iiiv aligns with the constraint point of the vertebra 166iiip. For example, the navigation system 20 moves the image of the vertebra 166iiiv from a position 166iiiva to an aligned position 166iiivb.

In one or more cases, the user 72 may create additional constraint points by touching other portions of the surface of the vertebra 166*iiip*. By selecting additional constraint points, the navigation system 20 constrains the surface of the image of the vertebra 166*iiiv* to the multiple constraint points, and moves the image of the vertebra 166*iiiv* such that the image of the vertebra 166*iiiv* aligns with the constraint points of the vertebra 166*iiip*. For the cases in which multiple images, for example the images of vertebra 166*iv*, 166*iiv*, and 166*iiiv*, are selected, the navigation system 20 may align the images as the navigation system 20 receives the constraint points.

In one or more other cases, subsequent to registering the image data and/or during a procedure, a user, such as the user 72, may select an image of the vertebra 166*iiiv* and may move the image of the vertebra 166*iiiv* to align the image of the vertebra 166*iiiv* with the physical position of the vertebra 166*iiip* of the patient 30. In one or more cases, to move the image of the vertebra 166*iiiv*, the user 72 may interact with the image of the vertebra 166*iiiv*, via watching the display 87 of the smartglasses 85, grabbing the image of the vertebra 166*iiiv*, and manipulating the image of the vertebra 166*iiiv* to align the image of the vertebra 166*iiiv* with the physical position of the vertebra 166*iiip*. Moreover, having approximately aligned the image of the vertebra 166*iiiv* with the physical position of the vertebra 166*iiip*, the image of the vertebra 166*iiiv* may be more accurately aligned via creating one or more constraint points with the tool 68, as discussed above. Accordingly, a discussion of creating one or more constrain points and aligning the image of the vertebra 166*iiiv* with the physical position of the vertebra 166*iiip* is not repeated.

In one or more other cases, the smartglasses 85 may display the one or more images, such that the user 72 can alternate between viewing 2-dimensional images, 3-dimensional images, x-ray images, pre-operative CT images, MRI, O-arm scans, or the like, thereby, allowing the user 72 to verify the alignment of the one or more images.

In one or more cases, the navigation system 20 and/or the smartglasses 85 may track the motion of one or more objects, such as the vertebra 166*iiip* of the patient 30. The smartglasses 85 may include an optical scanner configured to scan the field of view of the user and track the motion of one or more objects. The smartglasses 85 may be configured to track the shapes of one or more objects in real-time. In one or more cases, the navigation system 20 may compare one or more initial images of the position of one or more objects to one or more real-time images of the one or more objects acquired during the procedure. By comparing the one or more initial images to the one or more real-time images, the navigation system 20 may determine possible differences in location between the one or more objects when the image data was initially acquired and the real-time location of the one or more objects. In one or more cases, the one or more smartglasses 85 may capture the one or more real-time images, and transmit the one or more real-time images to the navigation system 20.

For the cases in which the navigation system 20 determines that an object moved or is displaced from the position of the registered image data, the navigation system 20 may send a message 173 to the one or more smartglasses 85, indicating that the object moved and/or is displaced. In other cases, the smartglasses 85 may detect motion or displacement, and may display the message 173. For example, the smartglasses 85 may display a message 173, such as "WARNING", on the display 87 of the smartglasses 85. In one or more cases, the smartglasses 85 may indicate the message by highlighting the related image 166*iiiv*. In one or more other cases, the smartglasses 85 may display the message 173 and highlight the related image. Having indicated a message that one or more objects are out of alignment, the work station 98 may automatically align the related one or more images. In one or more other cases, the user 72 may realign and/or make fine adjustments to the related one or more images, such as the image of the vertebra 166*iiiv*, as discussed herein.

In one or more cases, the navigation system 20 and/or smartglasses 85 may track the motion of one or more objects, such as the tissue 171*p*, surrounding one or more target objects, such as the vertebra 166*ip*, 166*iip*, and 166*iiip*. That is, the navigation system 20 and/or smartglasses 85 may track the motion of one or more target objects based on the motion one or more surrounding objects. By tracking surrounding objects, the navigation system 20 and/or smartglasses 85 may detect movement of the one or more target objects, and/or may preemptively detect movement of the one or more target objects based on detecting movement of the one or more surrounding objects. The surrounding tissue 171*p* may be, for example, a ligament used to connect a portion of the vertebrae of the spine. For the cases, in which the navigation system 20 determines that the one or more surrounding objects moved and/or is displaced, the navigation system 20 may send a message 173 to the one or more smartglasses 85 indicating that the one or more surrounding objects moved and/or is displaced. In other cases, the smartglasses 85 may detect motion or displacement, and may display the message 173. For example, the smartglasses 85 may display a message 173 as "WARNING" on the display 87 of the smartglasses 85. In one or more cases, the smartglasses 85 may indicate the message by highlighting the image of the tissue 171*v* related to the surrounding object, such as the tissue 171*p*. In one or more other cases, the smartglasses 85 may display the message 173 and highlight the related image. Having indicated a message that one or more objects are out of alignment, in one or more cases, the workstation controller 98 may automatically align the related one or more images. In one or more other cases, the user 72 may realign and/or make fine adjustments to the related one or more images, such as the image of the tissue 171*v*, as discussed herein. Alternatively, for the cases in which the user 72 knows that the one or more surrounding objects moved, such as when the tissue 171*p* is removed from the section of the spine 167, and that one or more objects, such as the vertebrae 166*ip*, 166*iip*, 166*iiip*, have not moved, the user may notify the navigation system 20 that the positions of the one or more objects are acceptable.

FIG. 4A illustrates an example of one or more sockets coupled with one or more spinous processes, respectively, and one or more trackers coupled with the one or more sockets. FIG. 4B illustrates an example tracker, such as tracker 179 coupled with an example socket, such as socket 175*a*. FIG. 4C is a flowchart illustrating an example alignment method 400.

In one or more cases, one or more sockets may be coupled to one or more objects at 402. At the beginning of a procedure, a user, such as user 72, may couple the one or more sockets, such as sockets 175*a*, 175*b*, 175*c*, 175*d*, 175*e*, and 175*f*, with one or more objects, such as vertebrae 166*ip*, 166*iip*, 166*iiip*, 166*ivp*, 166*vp*, and 166*vip*. A socket, such as socket 175*a*, may be coupled with a portion of the object, such as the spinous process 183 of the vertebra 166*vip*. In one or more cases, the socket 175*a* may be clamped to the spinous process 183. In one or more other cases, the socket 175*a* may be inserted into the spinous process 183. For example, an insertion end 188 of the socket 175*a* may have a sharp end configured to pierce bony anatomy, and the socket 175*a* may be hammered into the spinous process 183, via the insertion end 188 of the socket 175*a*. It is noted that the sockets 175*b*, 175*c*, 175*d*, 175*e*, and 175*f* may be coupled to the one or more objects in a similar manner as coupling the socket 175*a* to the respective object. Accordingly, a description of such features is not repeated.

Having coupled the one or more sockets to the respective objects, one or more trackers may be coupled to the one or more sockets at 404. In one or more cases, a tracker, such as tracker 179, may be coupled to a socket, such as socket 175*a*. The tracker 179 may include a socket tracking device 185 and a quick release end 187. The socket tracking device 185 may be configured to track the socket coupled with the tracking device 185 in a same or similar manner as the tool tracking device 66 is configured to track the tool 68. In one or more cases, the proximal end of the socket 175*a* includes a pin 191 that protrudes perpendicularly from an outer surface of the socket 175*a*. The quick release end 187 may include a track 193 that is configured to receive the pin 191 therein and removably couple the tracker 179 to the socket 175*a*.

The position of the tracker coupled with the socket may be determined at 406. In one or more cases, the user 72 may couple the tracker 179 to the socket 175*a*. The navigation system 20 and/or the one or more smartglasses 85 may locate the tracker 179 and determine the position of the socket 175*a* and/or the object, such as vertebra 166*vip*, based on the position of the tracker 179. For the cases in which the one or more smartglasses 85 locate the tracker 179, the one or more smartglasses 85 may transmit the location of the tracker 179 to the navigation system 20. The user may repeat this process of coupling the tracker 179 to each of the coupled sockets until the navigation system 20 determines the position of the sockets 175*b*, 175*c*, 175*d*, 175*e*, and 175*f*, and/or the position of the objects, such as vertebra 166*ip*, 166*iip*, 166*iiip*, 166*ivp*, and 166*vp*. In one or more cases, the user may sequentially couple the tracker 179 to each socket, and the navigation system 20 may determine the position of each socket and respective object. By determining the position of the objects, the navigation system 20 determines the alignment of the section of spine 167. In one or more other cases, during the beginning of the procedure, a tracker may be attached to each socket, and the navigation system 20 may determine the position of each socket and respective object. Having determined the position and alignment of each socket and respective object, all, one, or a few trackers may be removed before continuing the procedure.

In one or more cases, during the procedure in which all of the trackers are removed from the object space, the one or more smartglasses 85 may track the one or more objects of the subject 30 to determine if the one or more objects moved. For example, as a screw is being fastened to the vertebra 166*vip*, the navigation system 20 and/or the one or more smartglasses 85 tracks the vertebra 166*vip* and/or one or more of the adjacent vertebra to determine whether the vertebra 166*vip* moved. In one or more other cases, in which one or a few trackers remain attached to one or more sockets, the one or more smartglasses 85 may track the one or more trackers remaining in the object space and/or the one or more objects.

In one or more cases, one pair of smartglasses 85 may have one field of view that includes one or more objects, and one or more other pairs of smartglasses 85 may have other fields of view that includes one or more other objects. For example, a first pair of smartglasses 85 may have a field of view on vertebrae 166*vip*, 166*vp*, and 166*vip*, and a second pair of smartglasses 85 may have a field of view on vertebrae 166*ip*, 166*iip*, and 166*iiip*. The first pair of smartglasses 85 may acquire image data on the vertebrae 166*vip*, 166*vp*, and 166*vip* to determine whether one or more of the vertebrae 166*vip*, 166*vp*, and 166*vip* moved as discussed herein, and the second pair of smartglasses 85 may acquire image date on the vertebrae 166*ip*, 166*iip*, and 166*iiip* to determine whether one or more of the vertebrae 166*ip*, 166*iip*, and 166*iiip* moved as discussed herein. The image data acquired from both the first pair of smartglasses 85 and the second pair of smartglasses 85 may be compiled together by the navigation system 20 to whether one or more of the vertebrae moved during a procedure, for example, in a case where a procedure is performed on vertebrae 166*vip* and 166*vp*, and the navigation system 20 may determine that one or more of the vertebrae 166*ip*, 166*iip*, and 166*iiip* moved during the procedure.

In one or more cases, a determination is made at 408 as to whether the one or more objects are out of position. In one or more cases, the determination as to the position of the one or more objects may be preferably made by the one or more smartglasses 85. In one or more other cases, the determination as to the position of the one or more objects may be made by the EM system and/or the optical tracking system of the navigation system 20. In yet one or more other cases, the determination as to the position of the one or more objects may be made by the one or more smartglasses 85 and the EM system and/or the optical tracking system of the navigation system 20.

For the cases in which it is determined that the one or more objects are out of position (408: YES Branch), the one or more images of the one or more objects are realigned at 410. For example, the one or more smartglasses 85 may determine that a real world vertebra 166*vp* is out of position. In one or more cases, the one or more smartglasses 85 may determine that the vertebra 166*vp* is out of position by comparing an initial image of the vertebra 166*vp* to a real-time image of the vertebra 166*vp* that was acquired by the one or more smartglasses 85 during the procedure. The one or more smartglasses 85 may determine that the real-time image of the vertebra 166*vp* is in a position that is different from the position of the vertebra 166*vp* in the initial image. In one or more other cases, the one or more smartglasses 85 may acquire image data of the one or objects and transmit the image data in real-time to navigation system 20 to determine whether the one or more objects moved.

To realign the one or more images to the current position of the one or more objects, the user 72 attaches the tracker 179 to the socket that is attached to an object of an image that is out of alignment. The tracker 179 may be used as a reference frame for the object of the image that is out of alignment. For example, for the cases in which it is determined that the real-time image of the vertebra 166*vp* is out of position, the user 72 attaches the quick release end 187 of the tracker 179 to the pin 191 of the socket 175*a* that is coupled with the vertebra 166*vp*. The image of the one or more objects may be realigned as discussed herein. The tracker 179 may be subsequently attached to one or more other sockets, in which the image of the object attached to the socket is out of alignment. For example, the tracker 179 is coupled to another socket, such as socket 175*b*.

For the cases in which the navigation system 20 determines that the one or more objects are not out of position (408: NO Branch), the user 72 continues performing the procedure at 412, and a determination is made at 408 as to whether the one or more objects are out of position.

For the cases in which a procedure requires the socket and/or tracker 179 to be moved, for example, by moving the socket and/or tracker 179 from the spinous process 183 to a pedicle 181 of the vertebra 166*vip*, the user 72 may notify the navigation system 20 that the socket and/or tracker 179 will be moved. For example, in many spine surgeries, a laminectomy may be performed in which the spinous process is removed from the vertebra, thereby allowing the spinal cord to decompress and move away from a bulging disc. A laminectomy may be performed after one or more screws are placed into the pedicles of the vertebra.

Having notified the navigation system 20 that the tracker 179 will be moved, the tracker 179 may be removed from one portion of the object and moved into another portion of the same object. For example, if a user wanted to track the motion of the vertebra receiving the laminectomy, the user may attach the tracker 179 to a screw fastened to a pedicle 181 of the vertebra 166*vip*. The user may notify the navigation system 20 that the tracker 179 is being moved from the spinous process 183 to the screw positioned in the pedicle 181 of the vertebra 166*vip*. The user 72 may move the tracker 179 to the screw and indicate to the navigation system 20 that the tracker 179 is in a new position, which represents the same object, for example, vertebra 166*vip*. That is, the navigation system 20 may determine that the new position of the tracker is a shift in the frame of reference. By moving the tracker to a new position, the user 72 may perform additional procedures on the vertebra 166*vip*. For example, for the cases in which the user 72 is performing a decompression laminectomy, the tracker 179 may be moved to the socket 177 in the pedicle 181 so that the lamina may be removed from the vertebra 166*vip*.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A system for performing an image guided procedure in an operating theater, the system comprising:
    an imaging device configured to acquire first image data of at least one object of a subject, the subject being in a first position with respect to a first coordinate system;
    one or more smartglasses configured to acquire second image data of the at least one object of the subject with respect to a second coordinate system, the smartglasses including a localizer configured to track a position of at least one surgical tool or implant in a third coordinate system;
    a plurality of fiducial portions configured to facilitate registration of the first and second image data;
    a plurality of sockets incorporated into the plurality of fiducial portions, each said socket having a first end configured to be coupled to the at least one object of the subject and a second opposing end to which a tracker is removably coupleable;
    the tracker configured to be coupled to and decoupled from the second opposing end of each of the plurality of sockets; and
    the navigation system configured to (i) produce first registered image data by registering the first coordinate system and the second coordinate system of the first image data and second image data based on positions of the plurality of fiducial portions, (ii) produce second registered image data by transforming the first coordinate system of the first image data into a fourth coordinate system, and (iii) produce third registered image data by transforming the first coordinate system of the first image data into the third coordinate system of the localizer, the third and fourth coordinate systems being different than each other and registered to each other;
    wherein the one or more smartglasses are further configured to:
        display at least a portion of the first image data so as to be superimposed over the at least one object in an environment being viewed by a person using the smartglasses; and
        align the portion of the first image data which is displayed to correspond with a position of the at least one object using the plurality of fiducial portions; and
    wherein the navigation system is further configured to:
        obtain positions of the tracker while the tracker is coupled to the plurality of sockets at different times;
        determine a misalignment of a portion of the first image data to a current position of a respective socket of the plurality of sockets based on the positions of the tracker which were obtained; and
        cause the one or more smartglasses to re-align the portion of the first image data being displayed to the current position of the respective socket during performance of the image guided procedure.

2. The system of claim 1, further comprising a work station configured to receive the first image data and to obtain segments of the first image data.

3. The system of claim 1, wherein the smartglasses are configured to display at least one first segment of the first image data with a translucent or semi-translucent effect and at least one second segment of the first image data with an opaque effect.

4. The system of claim 1, wherein the smartglasses are further configured to display the superimposed registered image data as two-dimensional images or three-dimensional images.

5. The system of claim 1, wherein the smartglasses are further configured to acquire real time images of the at least one object of the subject and receive an input to re-align the superimposed first image data on the basis of the real time image of the at least one object.

6. The system of claim 5, wherein the input corresponds to one or more fiducial points on the at least one object.

7. The system of claim 6, wherein the smartglasses are configured to automatically re-align the superimposed first image data based on a second position of the subject and the one or more fiducial points on the at least one object.

8. The system of claim 5, wherein the input corresponds to a user gesture interacting with the at least one object.

9. A method for performing image guided procedures in an operating theater, the method comprising:
obtaining first image data of at least one object of a subject, the subject being in a first position with respect to a first coordinate system;
obtaining second image data of the at least one object of the subject with respect to a second coordinate system;
producing first registered image data by registering the first coordinate system and the second coordinate system of the first image data and the second image data based on positions of a plurality of fiducial portions;
producing second registered image data by transforming the first coordinate system of the first image data into a fourth coordinate system;
producing third registered image data by transforming the first coordinate system of the first image data into the third coordinate system of a localizer configured to track a position of at least one surgical tool or implant, the fourth coordinate system being different than the third coordinate system;
registering the third and fourth coordinate systems to facilitate tracking of the at least one surgical tool or implant in relation to the subject during the image guided procedure;
displaying at least a portion of the first image data so as to be superimposed over the at least one object in an environment being viewed by a person using smartglasses;
aligning the portion of the first image data which is displayed to correspond with a position of the at least one object using the plurality of fiducial portions;
obtaining positions of a tracker while the tracker is coupled to a plurality of sockets at different times;
determining a misalignment of a portion of the first image to a current position of a respective socket of the plurality of sockets based on the positions of the tracker which were obtained; and
causing a re-alignment of the portion of the first image data being displayed to the current position of the respective socket during performance of an image guided procedure.

10. The method of claim 9, further comprising segmenting the first image data, such that a user can select at least one of one or more superimposed images that corresponds to a segment of the first image data.

11. The method of claim 9, wherein the first image data is displayed in a translucent, semi-translucent, or opaque manner when superimposed over the at least one object in the environment being viewed by the person using smartglasses.

12. The method of claim 9, wherein the first image data comprises two-dimensional images or three dimensional images.

13. The method of claim 9, further comprising receiving an input to align image data.

14. The method of claim 13, wherein the input corresponds to one or more fiducial points on the at least one object.

15. The method of claim 13, wherein the input corresponds to a user gesture.

16. A computer program product, comprising:
a non-transitory computer-readable storage medium having program instructions embodied therewith for performing image guided procedures, the program instructions executable by one or more processors, the program instructions comprising:
obtaining first image data of at least one object of a subject;
obtaining second image data of the at least one object of the subject;
producing first registered image data by registering a first coordinate system and a second coordinate system of the first image data and the second image data based on positions of a plurality of fiducial portions;
producing second registered image data by transforming the first coordinate system of the first image data into a fourth coordinate system;
producing third registering image data by transforming the first coordinate system of the first image data into the third coordinate system of a localizer configured to track a position of at least one surgical tool or implant, the fourth coordinate system being different than the third coordinate system;
registering the third and fourth coordinate systems to facilitate tracking of the at least one surgical tool or implant in relation to the subject during the image guided procedure;
displaying at least a portion of the first image data so as to be superimposed over the at least one object in an environment being viewed by a person using smartglasses;
aligning the portion of the first image data which is displayed to correspond with a position of the at least one object using the plurality of fiducial portions;
obtaining positions of a tracker while the tracker is coupled to a plurality of sockets at different times;
determining a misalignment of a portion of the first image to a current position of a respective socket based on the positions of the tracker which were obtained; and
causing a re-alignment of the portion of the first image data being displayed to the current position of the respective socket during performance of an image guided procedure.

17. The computer program product of claim 16, wherein the program instructions further comprise receiving an input to align images.

18. The computer program product of claim 17, wherein the input corresponds to a user gesture.

* * * * *